(12) United States Patent
Lavergne et al.

(10) Patent No.: US 8,153,704 B2
(45) Date of Patent: *Apr. 10, 2012

(54) POLYMER CEMENT FOR PERCUTANEOUS VERTEBROPLASTY AND METHODS OF USING AND MAKING SAME

(75) Inventors: Claudine Lavergne, Caixon (FR); Alain Leonard, Caixon (FR)

(73) Assignee: Teknimed, Vic-En-Bigorre (FR)

( * ) Notice: Subject to any disclaimer, the term of this patent is extended or adjusted under 35 U.S.C. 154(b) by 26 days.

This patent is subject to a terminal disclaimer.

(21) Appl. No.: 11/757,427

(22) Filed: Jun. 4, 2007

(65) Prior Publication Data

US 2008/0044374 A1    Feb. 21, 2008

Related U.S. Application Data

(63) Continuation-in-part of application No. 10/871,036, filed on Jun. 21, 2004.

(30) Foreign Application Priority Data

Jun. 22, 2004 (FR) .................................. 04 05249

(51) Int. Cl.
*A61L 27/18* (2006.01)
*A61F 2/00* (2006.01)
(52) U.S. Cl. ......... 523/117; 523/115; 523/116; 424/423
(58) Field of Classification Search ................. 523/117, 523/116
See application file for complete search history.

(56) References Cited

U.S. PATENT DOCUMENTS

| | | | | |
|---|---|---|---|---|
| 5,795,922 | A * | 8/1998 | Demian et al. ............... | 523/117 |
| 5,902,839 | A * | 5/1999 | Lautenschlager et al. .... | 523/115 |
| 6,309,420 | B1 * | 10/2001 | Preissman ................. | 623/16.11 |
| 7,008,433 | B2 | 3/2006 | Voellmicke et al. ........... | 606/93 |
| 2003/0031698 | A1 | 2/2003 | Roeder et al. ................ | 424/423 |
| 2005/0119746 | A1 * | 6/2005 | Lidgren ..................... | 623/17.11 |
| 2005/0255159 | A1 * | 11/2005 | Hyers et al. ................. | 424/484 |
| 2007/0027230 | A1 | 2/2007 | Beyar et al. ................. | 523/117 |

FOREIGN PATENT DOCUMENTS

| | | | |
|---|---|---|---|
| CA | 2158402 | * | 3/1996 |
| EP | 1 595 553 | | 11/2005 |
| WO | WO 02/064062 | | 8/2002 |
| WO | WO 2004/103420 | | 12/2004 |

OTHER PUBLICATIONS

Carrodeguas et al., "Injectable Acrylic Bone Cements For Vertebroplasty With Improved Properties"; XP-002312783, *Journal of Biomedical Materials Research*, Wiley, New York, NY, US, vol. 68, No. 1, Jan. 15, 2004, pp. 94-104.
Search Report, 2008.
Jasper et al., "Material Properties of Various Cements for Use with Vertebroplasty", XP-002312782, *Journal of Material Science: Materials in Medicine*, 13(1):1-5 (2002).
Mathis et al., Percutaneous Vertebroplasty: A Developing Standard of Care for Vertebral Compression Fractures, XP-002312784, *American Journal of Neuroradiology.*, 22:373-381 (2001).

\* cited by examiner

*Primary Examiner* — Tae H Yoon
(74) *Attorney, Agent, or Firm* — Mintz Levin Cohn Ferris Glovsky and Popeo PC

(57) ABSTRACT

The invention provides a fluid cement for medical use for bone reconstruction, in particular for filling the vertebral body, and a binary composition which is intended for the preparation of such a cement. The invention also provides a device for conditioning the binary composition, and a method of preparing a bone cement from a binary composition. The fluid cement according to the invention comprises: a) approximately 60% to 85% by weight of a polymer comprising a polymethylmethacrylate and a methylmethacrylate monomer and b) approximately from 15 to 40% by weight of a radio-opaque composition. Preferably, the radio-opaque composition comprises a radio-opacifier, such as barium sulfate and zirconium dioxide, in a mixture with a calcium phosphate, for example apatite hydroxide.

9 Claims, 2 Drawing Sheets

POLYMER CEMENT FOR PERCUTANEOUS VERTEBROPLASTY AND METHODS OF USING AND MAKING SAME

RELATED APPLICATIONS

This application is a continuation-in-part of U.S. Ser. No. 10/871,036, filed on Jun. 21, 2004, which claims the benefit of priority of French Application No. 04 05249, filed on May 14, 2004, both of which are incorporated herein, in their entireties.

FIELD OF THE INVENTION

The present invention relates to the field of polymeric cements, in particular acrylic cements, used for repairing bone and joint traumas. The subject thereof is a fluid cement for medical use in bone reconstruction, in particular for filling the vertebral body, and also a binary composition intended for the preparation of such a cement. Another subject of the present invention is a conditioning device for said binary composition. A method of preparing bone cement from a binary composition is likewise claimed.

BACKGROUND OF THE INVENTION

Bone cements have been used for a number of years in order to assist the attachment of artificial implants to the skeleton. The cement which serves as a junction between the bone and the implant must meet a certain number of requirements, in particular mechanical, but must also be non-toxic and biocompatible. Certain cements have even been studied for their bioactive properties, i.e. for their action which assists the adhesion and the cellular growth on the implant.

In the United States, between 400,000 and 500,000 clinical osteoporotic vertebral fractures occur annually. Approximately one third of these patients develop chronic, debilitating pain that does not respond to conservative treatment. For many people, this represents the end of their independent lifestyle, sometimes leading to a worse than expected overall survival rate.

Many of these patients can be effectively treated by the percutaneous injection of bone cement into the fractured vertebral body. This procedure results in significant reduction in pain in approximately 80% of patients treated by vertebroplasty, in addition to strengthening of the diseased bone.

Since the mid 1980's, the use of cements has widened to bone repair, and primarily to percutaneous vertebroplasty. This minimally invasive technique allows injection of a cement through a trocar into a fractured vertebra in order to ensure bone volume and stabilization. The first percutaneous vertebroplasty was achieved in 1984 and has since enjoyed increasing success, opening the way to plastic repair of other types of bone.

Vertebroplasty is a minimally invasive surgical technique that has been introduced to medically manage vertebral compression fractures. In this procedure, bone cement is injected percutaneously, through a long cannula and into the vertebral cancellous bone. Once hardened, the cement reinforces mechanically the weakened vertebra. The principal benefit of this procedure is that up to 90% of the patients experience pain relief within 24 Hours. (Jensen, M. E. et al. (1997). *Am J Neuroradiol* 18: 1897-1904.) The procedure aims to augment the weakened vertebral body and stabilize it. A dough of an injectable bone cement is carefully injected directly into the fractured vertebral body.

Even if this procedure is gaining acceptance, there is still concern regarding accompanying risks. In particular, extraosseous cement leakage, which occurs in up to 73% of the procedures can cause significant side effects. (Barragan-Campos, H. M., et al. (2006). Radiology 238(1): 354-62). This is currently one of the most serious complications. Leaks occur through a path caused by irregularities in the structure, such as blood vessels and/or damage to the vertebral wall. Ideally, the cement should be of moderate viscosity in order to uniformly infiltrate the trabecular bone skeleton, thereby flow paths caused by irregularities.

The cements which have been used to date are organic polymers, formed from a mixture of a prepolymer, generally PMMA (methyl polymethylmethacrylate) and from a monomer, generally MMA (methyl methylmethacrylate), reacting in the presence of a polymerization activator. For use in vivo, which does not allow high temperatures, a reaction initiator is added.

Most commercially available cements are available in the form of two separate components: a powder comprising principally prepolymer balls and a liquid containing principally the monomer. The initiator, for example benzoyl peroxide (BPO), is generally incorporated with the powder, while the liquid contains a chemical activator (catalyst), such as dimethylparatoluidine (DMPT), the polymerization reaction starting when the two components are mixed. In order to avoid spontaneous polymerization which can possibly occur during storage, there is incorporated furthermore in the liquid component a stabilizer, commonly hydroquinone. The activator and the initiator are introduced in the proportion of 1 to 2% in the corresponding component, the stabilizer itself taking effect at some tens of ppm.

In order to display the cement visually during and after the operation by radiological means, a radio-opaque substance can be added, most often barium sulfate ($BaSO_4$) or zirconium dioxide ($ZrO_2$). Commercial cements contain a quantity thereof of the order of 10% in the powder.

These binary compositions for the preparation of bone cements, designed originally for attachment of implants and sealing of prostheses, fulfill the criteria of resistance to traction and to compression, of chemical neutrality and of biocompatibility. They are authorized for medical use and have proved their qualities in the long term when the skeleton is subjected to large, repeated forces. This is why bone cements for attaching implants have been adopted as the preferred material for bone reconstruction surgery.

However, the conditions for using cements in percutaneous surgery requires different properties to prevent accidents, the effects of which can be dramatic for the patient, such as paraplegia. The practitioner must use a cement which is sufficiently fluid for it to flow through a trocar with a diameter of a few millimeters, and for it to maintain this fluidity long enough for the practitioner to have the time to operate at leisure. At the same time, the physical characteristics of the cement after polymerization must be preserved.

Further, the cement injected even in small quantities must be visually displayed during the operation. The currently marketed compositions do not have this property. Although certain cements contain a radio-opacifier, correct visual display during percutaneous injection is not obtained. This leads the practitioners to modify the compositions themselves, with the risk of modifying, at the same time, the physical characteristics of the cement, in particular its viscosity and its rate of hardening, and its resistance properties after polymerization.

Hence, the currently known cements, even if they are efficient in attaching implants to the skeleton, have not been designed for a treatment stabilizing the vertebral body by a percutaneous route and do not take into account the specificities connected to this technique.

SUMMARY OF THE INVENTION

The object of the present invention is to provide a material suitable for percutaneous surgical use, in particular for filling the vertebral body, said material having a suitable intra-operative and post-operative behavior i.e.: fluidity, setting time greater than 15 minutes, opacity during fluoroscopy, resistance to compression: at least 70 Mpa, resistance to bending: at least 50 Mpa, flexural modulus: at least 1,800 Mpa. Of course, such a cement must be compatible with medical use from the point of view of its toxicity and its biocompatibility.

Unexpectedly, it was found that it was possible to formulate a cement based on polymethylmethacrylate and methylmethacrylate monomer fulfilling the specifications above, by incorporating in said cement high quantities of a radio-opaque composition, without the qualities demanded for intended use being altered.

More precisely, the subject of the present invention is a fluid cement for medical use for filling the vertebral body, comprising:

a) approximately 60% to 85% by weight of a polymer comprising a polymethylmethacrylate and a methylmethacrylate monomer, and b) approximately from 15% to 40% by weight of a radio-opaque composition.

In one embodiment of the invention, the radio-opaque composition comprises a radio-opaque compound and calcium phosphate. Optionally, the radio-opaque compound comprises approximately 18% to 37% by weight of the fluid cement and/or the calcium phosphate comprises approximately 3% to 10% by weight of the fluid cement. Preferably, the radio-opaque compound comprises about 20%, 27% or 34% by weight of the fluid cement. Preferably, the calcium phosphate comprises about 3%, 4% or 6% by weight of the fluid cement. Optionally, the radio-opaque compound is barium sulfate or zirconium dioxide and/or the calcium phosphate is apatite hydroxide.

In one aspect of this embodiment of the invention, the polymethylmethacrylate and the methylmethacrylate monomer are introduced in a weight ratio between 1 and 2. Preferably, the polymethylmethacrylate and the methylmethacrylate monomer are introduced in a weight ratio between 1.4 and 1.6.

In another aspect of this embodiment of the invention, the fluid cement further includes an effective quantity of one or more of the reagents selected from the group consisting of: a chemical polymerization activator, a polymerization initiator and a stabilizer. Optionally, the chemical polymerization activator is dimethylparatoluidine, the polymerization initiator is benzoyl peroxide and/or the stabilizer is hydroquinone.

The invention also provides a binary composition intended for preparation of a bone cement composed of a liquid component L comprising a methylmethacrylate monomer and a powder component P comprising a polymethylmethacrylate, characterized in that the powder component P comprises approximately from 25% to 60% by weight relative to the weight of powder of a radio-opaque composition. Preferably, the powder component P comprises between approximately 35% and 50% by weight relative to the weight of powder of a radio-opaque composition.

In one embodiment of the invention, the radio-opaque composition comprises a radio-opaque compound and calcium phosphate. Optionally, the radio-opaque compound comprises approximately 25% to 50% by weight of the powder component and/or the calcium phosphate comprises approximately 4% to 12% by weight of the powder component. Preferably, the radio-opaque compound comprises about 27% or 45% by weight of the powder component. Preferably, the calcium phosphate comprises about 5% or 9% by weight of the powder component. Optionally, the radio-opaque compound is barium sulfate or zirconium dioxide and/or the calcium phosphate is apatite hydroxide.

In one aspect of this embodiment of the invention, the binary composition further includes an effective quantity of a chemical polymerization activator in the liquid component L, a polymerization initiator in the powder component P and/or a stabilizer. Optionally, the chemical polymerization activator is dimethylparatoluidine, the polymerization initiator is benzoyl peroxide and/or the stabilizer is hydroquinone. Optionally, the powder component P and the liquid component L are in a weight ratio P/L between 1 and 2. Preferably, the powder component P and the liquid component L are in a weight ratio P/L between 1.4 and 1.6.

The invention also provides a device intended for preparation of a fluid cement for medical use from a binary composition characterized in that it comprises: i) a first receptacle containing the liquid component L, and ii) a second receptacle containing the powder component P. The invention also provides a fluid cement for medical use for filling the vertebral body prepared by means of this device.

The invention also provides a method of preparing a fluid cement, for medical use, for filling the vertebral body, comprising essentially the step consisting in mixing the components made of powder P and liquid L into a homogeneous mass. Optionally, the powder component P and the liquid component L are provided in a weight ratio P/L between 1 and 2. Preferably, the powder component P and the liquid component L are provided in a weight ratio P/L between 1.4 and 1.6. The invention also provides a fluid cement for medical use for filling the vertebral body prepared by means of this method.

BRIEF DESCRIPTION OF THE DRAWINGS

The appended drawings of the figures are presented to further describe the invention and to assist in its understanding through clarification of its various aspects.

DETAILED DESCRIPTION OF THE INVENTION

Figure 1:
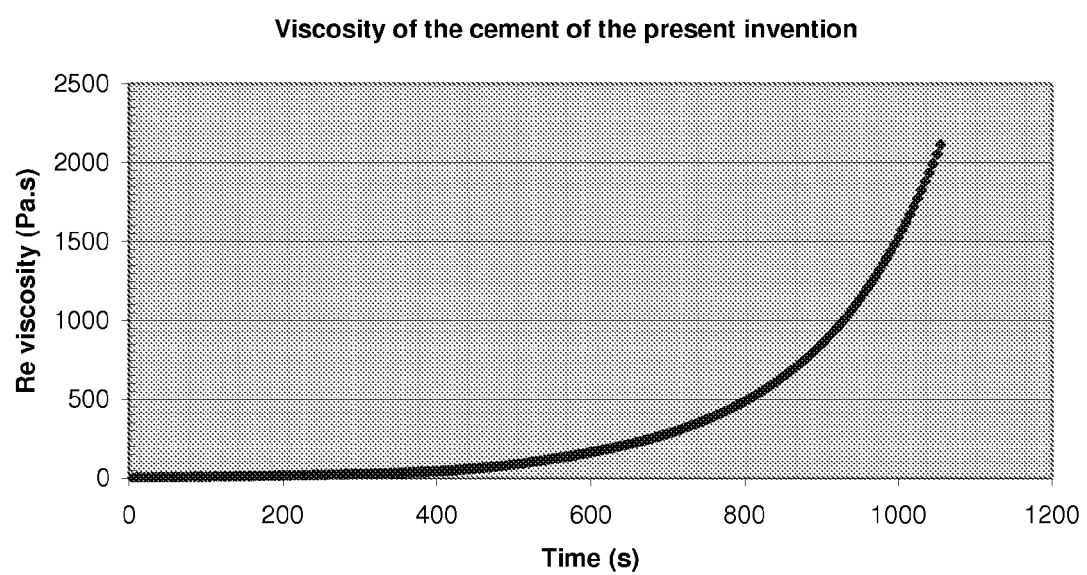
FIG. 1 is a graph showing the viscosity of a bone cement of the invention from mixing of the cement over time.

The cement according to the invention has good fluidity in the minutes following the bringing together of the ingredients, the component, and can be worked with up to 10 minutes and more after its preparation. The polymerization reaction causes the mass setting of the polymethylmethacrylate and of the monomer which disappear in order to form a solid polymer cement. In the present application, the term "cement" or "fluid cement" corresponds to the cement as occurs after mixing the ingredients. The composition of the cement will be considered as that of the fluid cement which is ready for use, before solidification. Additional objects and advantages afforded by the present invention will be apparent from the detailed description and exemplification hereinbelow.

One embodiment of the present invention is to provide a cement suitable for percutaneous surgical use wherein the cement makes it easier for a physician to detect leaks upon administration of the cement to a subject. One example of such a cement of the present invention is one which contains a very high amount of radio opaque agent. For example, the leak detecting cement contains 50% by weight of radio opaque cement. In other examples of the leak detecting cement of the invention, 50, 55, 60, 65, 70, 75 and 80% of the cement is made up of radio opaque agent, by weight. The use of a high percentage of radio opaque material allows the cement to be well visualized. The leak detecting cement must indeed be well visualised during the injection procedure in order to highlight the cement flow and then avoid undesired leaks.

The radio opaque compound is preferably zirconium oxide, well known to be compatible with medical use. The radio opaque compound is optionally barium sulfate. In another embodiment, the radio opaque compound further comprises a the radio-opacifier calcium phosphate mixed with the radio opaque material.

The present invention also provides a cement with a medium viscosity suitable for percutaneous surgical use. This cement reduces leaks when it is administered to a subject. The cement of this embodiment of the present invention comprises a high amount of radio opaque agent. For example, the cement contains 30% by weight of radio opaque material. In other examples of the cement of the invention, 35, 40, 45, 50, 55, 60, 65, 70, 75 and 80% of the cement is made up of radio opaque agent, by weight. The cement of this embodiment is well visualised during the injection procedure in order to highlight the cement flow and then avoid undesired leakages.

The radio opaque compound can comprise a mixture with the radio-opacifier calcium phosphate. The radio opaque material is preferably barium sulfate or zirconium oxide.

The invention also provides methods for the prevention of leaks of bone cement when administered to a subject. The method includes injecting the cement when in a dough stage into the vertebral body. In order to practice this method, the cement must have a long injection time to give the physician sufficient time to inject it safely. The cement will then spread more uniformly than when a low viscosity bone cement is used that has shorter injection time and needs to be injected in its fluid stage and then follow the path of least resistance. The long polymerization times of the cements of the current invention, allow physicians to use longer injection times, thus decreasing the chances of leakage.

Polymethylmethacrylate (or PMMA) and methylmethacrylate monomer (or MMA) which go into the composition of the cement according to the invention, are those commonly used for the preparation of acrylic cements. The PMMA powders occur in the form of polymer balls. The molar mass of these powders is between 150,000 and 1,500,000 g/mol. The average diameter of the particles is between 30 µm and 100 µm. The monomer is the methylic ester of methacrylic acid. MMA and PMMA for medical use are commercially available.

The radio-opaque composition represents a large fraction of the cement. It has the aim of allowing injection of the cement under continuous control by fluoroscopy, in particular during vertebroplasty procedures. It can be formed by a pure radio-opaque compound or as a mixture with other ingredients. It has been found that the combination of a calcium phosphate and a radio-opaque compound allowed a cement to be obtained which was readily visible during its positioning and subsequently well tolerated by the organism. Advantageously, the radio-opaque composition present in the cement according to the invention comprises a radio-opaque compound and calcium phosphate.

The recommended usage proportions of the radio-opaque compound and of the calcium phosphate, by weight relative to the total weight of the cement, are such that said radio-opaque composition comprises approximately 15% to 40% of a radio-opaque compound and approximately 3% to 10% of calcium phosphate. Preferably, the radio-opaque composition comprises approximately 20%, 27% or 34% of a radio-opaque compound and approximately 3%, 4% or 6% of calcium phosphate.

The radio-opaque compound can be chosen from compounds which are known and compatible with medical use. Said compound is preferably chosen within the group composed of barium sulfate and zirconium dioxide. Barium sulfate ($BaSO_4$) is a radio-opacifier commonly used in cements for implant attachment, the innocuousness of which is recognized. It occurs in general in the form of powder, the particles of which have an average diameter of 1 to 10 µm. Zirconium dioxide ($ZrO_2$) can be used alternatively. It is introduced in the form of powder, the particles of which have an average diameter of 20 µm.

The radio-opaque composition can comprise a mixture with the radio-opacifier, calcium phosphate. Advantageously, the calcium phosphate is apatite hydroxide. Advantageously, there can be used a phosphocalcic hydroxyapatite of the formula $Ca_{10}(PO_4)_6(OH)_2$, with a Ca/P ratio of 1.667 and a granulometry less than 30 µm. The introduction of this ingredient into the composition brings a doubly beneficial effect, on the one hand by improving the homogeneity of the cement and consequently its malleability, and on the other hand by increasing its biocompatibility. In fact, it is known that hydroxyapatite assists the bone regrowth by stimulating the biological activity of the osteoblasts and their proliferation. It has been studied for this reason without regard to the advantages of its mechanical properties.

The introduction into the cement of a large quantity of opacifying composition has repercussions on its physical and chemical characteristics, in particular its fluidity, its solidification rate and its mechanical resistance. In order to obtain optimal functional properties it is recommended to keep to the proportions of ingredients as defined by the present application, and which are likewise the subject of the present invention.

In particular, in the cement according to the invention, polymethylmethacrylate and methylmethacrylate monomer are advantageously provided in a weight ratio between 1 and 2. Preferably, the ratio PMMA/MMA is between 1.4 and 1.6. Hence, surprisingly, it has been determined that the optimal formulation is the one where the proportion of PMMA is less than in standard formulations, the addition of the opacifying composition being essentially to the detriment of the polymethylmethacrylate.

The cement according to the invention can finally contain a certain number of reagents assisting the control of the polymerization. In particular, it can comprise, in addition to the ingredients mentioned above, an effective quantity of one or more of the following reagents: a chemical polymerization activator, a polymerization initiator, a stabilizer. The person skilled in the art knows these reagents and has mastered their use.

A reaction initiator can advantageously be chosen among the polymerization catalysts, such as benzoyl peroxide (BPO). The activator or accelerator of the polymerization reaction is preferably N,N-dimethylparatoluidine (DMPT). The stabilizer, preferably hydroquinone, can be added in order to avoid premature polymerization of the monomer as a result of exposure to heat or light. These reagents are effective in very small concentrations which the person skilled in the art can adjust as a function of the desired kinetics. They go into the composition of the cement in quantities of the order of 0.2% to 2% for benzoyl peroxide, of 1.5% to 2.5% for DMPT, and approximately 20 ppm as far as hydroquinone is concerned. According to a preferred formulation, there is used 0.4% to 0.6% of benzoyl peroxide; 2.4% of DMPT and 20 ppm of hydroquinone.

The cement according to the invention, once ready, will react in order to form a solid mass in a relatively short period of time (a few minutes to a few tens of minutes), the formulation claimed here setting at the earliest in 15 minutes. It is evident that the ingredients reacting together must be mixed solely at the moment of use. This is why it is convenient to use two pre-mixtures of ingredients which it suffices to bring together in order to prepare the cement according to the invention. These pre-mixtures, one in powder form, the other in liquid form, form the two components of a binary composition which is intended for the preparation of a bone cement according to the invention.

According to the invention, said binary composition is composed of a liquid component L comprising a methylmethacrylate monomer and a powder component P comprising a polymethylmethacrylate, in which the powder component P comprises approximately 25 to 60% by weight relative to the weight of powder of a radio-opaque composition.

Advantageously, in the binary composition according to the invention, the powder component P comprises at least approximately 35%, preferably at least approximately 50% by weight relative to the weight of powder of a radio-opaque composition.

According to an interesting feature of the invention, said radio-opaque composition comprises a radio-opaque compound and calcium phosphate. Advantageously, the radio-opaque composition comprises approximately 25% to 50% of a radio-opaque compound and approximately 4% to 12% of calcium phosphate, by weight relative to the weight of powder. According to a preferred formulation, the radio-opaque composition comprises approximately 27% or 45% of a radio-opaque compound and approximately 5% or 9% of calcium phosphate, by weight relative to the weight of powder.

Said radio-opaque compound can be chosen within the group composed of barium sulfate and zirconium dioxide. As far as calcium phosphate is concerned, apatite hydroxide is chosen preferably.

The binary composition according to the invention comprises in addition preferably an effective quantity of one of more of the following reagents:

in the liquid component L, a chemical polymerization activator;
in the powder component P, a polymerization initiator and a stabilizer.

For example, the liquid component L can comprise from 1.5% to 2.5% of DMPT. The powder component P can comprise from 0.2% to 2% of benzoyl peroxide and 20 ppm of hydroquinone. Preferably, the liquid component L contains 2.4% of DMPT, whilst the powder component P contains 0.5.+/−.0.1% of PBO.

During use in the operating theatre, the two components, powder and liquid, are mixed. At this moment, the powder phase dissolves into the liquid phase, thus giving a mixture which must be sufficiently fluid to be able to be injected into a vertebral body. In the course of the mixing, the activator and the initiator react in order to produce free radicals. These radicals initiate the polymerization reaction which leads to progressive hardening of the cement, according to the desired kinetics. For good control of these criteria, the binary composition according to the invention is advantageously formulated such that the powder component P and the liquid component L are in a weight ratio P/L between 1 and 2, preferably between 1.4 and 1.5.

For practitioners, it is imperative to limit manipulations which are lengthy and a source of errors to the moment of operating. This is why it is convenient to use pre-mixtures of ingredients in separate receptacles. Another subject of the present invention is therefore a device which is intended for the preparation of a fluid cement for medical use according to the invention comprising:

i) a first receptacle containing a liquid component comprising at least one monomer of methylmethacrylate and possibly an effective quantity of a chemical polymerization activator, preferably dimethylparatoluidine;

ii) a second receptacle containing a powder component comprising at least one polymethylmethacrylate and a radio-opaque composition, as described above, and possibly an effective quantity of a polymerization initiator, preferably benzoyl peroxide and a stabilizer, preferably hydroquinone.

In other words, a device is claimed which is intended for the preparation of a fluid cement for medical use from a binary composition according to the invention, comprising:

i) a first receptacle containing the liquid component L, and
ii) a second receptacle containing the powder component P.

The device according to the invention can be used advantageously for the preparation of a fluid cement for medical use for filling the vertebral body.

Another subject of the present invention is a method of preparing a fluid cement for medical use for filling the vertebral body, comprising essentially the step consisting in mixing into a homogeneous mass a powder component P and a liquid component L, as are described above. According to an advantageous variant of the claimed method, the powder component P and the liquid component L are introduced in a weight ratio P/L between 1 and 2. Preferably, the components P and L are provided in a weight ratio P/L between 1.4 and 1.5.

The method according to the invention can be implemented advantageously for the preparation of a fluid cement for medical use for filling the vertebral body.

The following examples will allow better comprehension of the invention without in any way limiting the scope thereof.

EXAMPLES

Abbreviations

PMMA: polymethylmethacrylate
MMA: methyl methacrylate
BPO: benzoyl peroxide
$BaSO_4$: barium sulfate
$ZrO_2$: zirconium dioxide
HAP: phosphocalcic hydroxyapatite
DMTP: dimethylparatoluidine
HQ: hydroquinone
P/L: ratio of powder phase/liquid phase, by weight.

Example 1

Binary Composition 1

| POWDER PHASE (% by weight) | |
|---|---|
| PMMA: | 64.41 |
| BPO: | 0.59 |
| $BaSO_4$: | 25.00 |
| HAP | 10.00 |
| LIQUID PHASE (% by weight) | |
| MMA: | 97.60 |
| DMPT: | 2.40 |
| HQ: | 0.002 | with P/L = 1.41

Example 2

Binary Composition 2

| POWDER PHASE (% by weight) | |
|---|---|
| PMMA: | 59.33 |
| BPO: | 0.54 |
| ZrO$_2$: | 30.08 |
| HAP: | 10.05 |
| LIQUID PHASE (% by weight) | |
| MMA: | 97.60 |
| DMPT: | 2.40 |
| HQ: | 0.002 | with P/L = 1.57

Example 3

Binary Composition 3

| POWDER PHASE (% by weight) | |
|---|---|
| PMMA: | 49.43 |
| BPO: | 0.45 |
| ZrO$_2$: | 40.01 |
| HAP: | 10.11 |
| LIQUID PHASE (% by weight) | |
| MMA: | 97.60 |
| DMPT: | 2.40 |
| HQ: | 0.002 | with P/L = 1.47

Example 4

Binary Composition 4

| POWDER PHASE (% by weight) | |
|---|---|
| PMMA: | 49.50 |
| BPO: | 0.45 |
| ZrO$_2$: | 45.06 |
| HAP: | 4.99 |
| LIQUID PHASE (% by weight) | |
| MMA: | 97.60 |
| DMPT: | 2.40 |
| HQ: | 0.002 | with P/L = 1.48

Example 5

Method of Preparing a Bone Cement

Powder Component:

The powder phase is obtained by screening the various ingredients at 200 μm, then mixing by agitation for one minute, for example in a multiflux mixer.

Liquid Component:

The liquid phase is prepared by dissolving hydroquinone in the monomer MMA. The agitation is maintained until complete dissolution. DMPT is then added.

The two phases are conditioned separately in receptacles suitable for their preservation. The instantaneous preparation kits comprise a receptacle containing the liquid phase and a receptacle containing the powder phase.

Binary Composition

During use in the operating theatre, the receptacles are opened and their contents are mixed. The powder dissolves rapidly into the liquid phase giving a fluid mixture which is injected into the vertebral body of the patient through an adequate tube. The initiator BPO and the activator DMPT react to form free radicals which initiate the progressive polymerization reaction of the cement. The surgeon then has about fifteen minutes to operate, controlling the procedure permanently by fluoroscopy.

Example 6

Preparation of Hydroxyapatite

The hydroxyapatite which is used is obtained by precipitation in an aqueous medium. This method is based on neutralization of orthophosphoric acid by calcium hydroxide, as described by Wallaeys (Wallaeys R., 1952 Ann. Chim., 7, pp. 808-848) and repeated by Osaka (Osaka A., et al., 1991, J. Mater. Sci. Mat. Med., 2, pp. 51-55). The reaction which is initiated is the following:

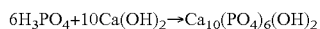

$$6H_3PO_4 + 10Ca(OH)_2 \rightarrow Ca_{10}(PO_4)_6(OH)_2$$

This little used method has the huge advantage of being non-polluting because the reaction medium is demineralized water. The reaction does not generate any toxic component which risks impairing the biocompatibility of the bone cement.

The method of fabrication takes place in the following manner:

After calcination at 900° C., the calcium hydroxide is suspended in demineralized water, to which a solution of diluted phosphoric acid is added. After maturation, the reaction product is filtered, dried in an oven, then ground and screened with various screens. Then the thus obtained powder is calcinated at a temperature between 900° C. and 1100° C. A final screening allows the fraction of a granulometry less than 30 μm to be recovered.

Example 7

ISO Standard Tests

Standard ISO 5833, entitled, "Surgical implants, implants based on acrylic resin" defines the characteristics required by regulations and the standard tests allowing these characteristics to be quantified. The compositions described in examples 1 to 4 above were tested.

A first series of tests relates to the properties of the cement during use, i.e. the setting time, the maximum temperature achieved by the cement during polymerization, and the kneading time. The results obtained for the four compositions are presented in Table 1.

A second series of tests relates to the properties of the installed cement, i.e. the resistance to compression, the resistance to bending and the flexural modulus. The results obtained with the compositions 1, 3 and 4 are presented in Table 2.

All the operating modes are described in detail in the standard ISO 5833.

TABLE 1

|  | setting time (mn) | max. temperature (° C.) | kneading time (mn) |
|---|---|---|---|
| Composition 1 | 17.80 | 73.9 | 10.75 |
| Composition 2 | 15.66 | 73.3 | 10.20 |
| Composition 3 | 18.46 | 67.9 | 9.50 |
| Composition 4 | 18.05 | 69.5 | 9.00 |

TABLE 2

|  | resistance to compression (Mpa) | resistance to bending (Mpa) | flexural modulus (Mpa) |
|---|---|---|---|
| Composition 1 | 84.2 | 58.2 | 3345 |
| Composition 3 | 88.4 | 58.1 | 4043 |
| Composition 4 | 74.6 | 57.6 | 3461 |

The obtained results show that the cements according to the invention are in accordance with regulations in strength and can be used as surgical implants.

It is noted likewise that their characteristics fulfill the specifications defined above for cements which can be used in percutaneous vertebroplasty (setting time greater than 15 minutes), opacity during fluoroscopy, with the retention of the characteristics of resistance to compression, resistance to bending and flexural modulus.

Example 8

Leak Detecting Composition

| POWDER PHASE (% by weight) 27.2 g | |
|---|---|
| PMMA: | 49.5 |
| BPO: | 0.5 |
| ZrO$_2$: | 45.0 |
| Hap: | 5.0 |
| LIQUID PHASE (% by weight) 9.2 g | |
| MMA: | 99.0 |
| DMPT: | 1.0 |
| HQ: | 0.002 |

P/L = 1.03

The cement of the present invention becomes injectable five minutes after mixing the powder and the liquid phase. The viscosity of the bone cement is at least equal to 40 Pa·s. The viscosity then remains less than 1500 Pa·s during the injection period which can last at least 16 minutes after the start of mixing, as shown in FIG. 1.

Example 9

Medium Viscosity Composition

| POWDER PHASE (% by weight) 22 g | |
|---|---|
| PMMA: | 63.1 |
| BPO: | 0.5 |
| BaSO4$_2$: | 27.4 |
| HAP: | 9.0 |
| LIQUID PHASE (% by weight) 9.2 g | |
| MMA: | 98.5 |
| DMPT: | 1.5 |
| HQ: | 0.002 |

Figure 2:
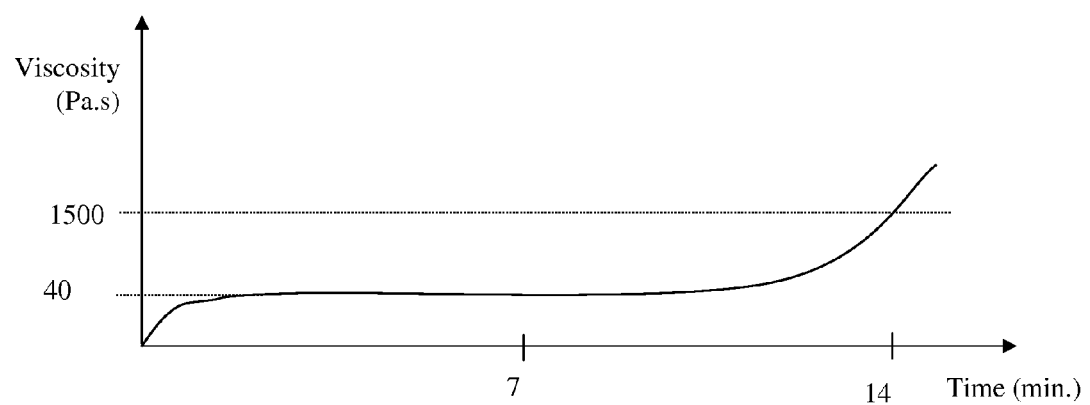
FIG. 2 is a graph showing the viscosity of a bone cement of the invention from mixing of the cement over time.

This cement becomes injectable one minute after mixing the powder and the liquid phase. The viscosity of the bone cement is at least equal to 40 Pa·s. The viscosity then remains less than 1500 Pa·s during the injection period which can last at least 14 minutes after the start of mixing, as shown in FIG. 2.

We claim:

1. A polymer cement kit for bone filling comprising:
   a) a receptacle comprising liquid components L, wherein the liquid components comprise a methylmethacrylate monomer (MMA), and
   b) a receptacle comprising powder components P, wherein the powder components comprise a polymer component comprising polymethylmethacrylate homopolymer (PMMA) and at least 35% of a radio-opaque composition, wherein the radio-opaque composition comprises 25-50% of a radio-opaque compound and 4-12% calcium phosphate relative to the weight of the powder component P;
   wherein the powder component P and the liquid component L are provided in a weight ratio P/L between 1.4 and 1.6.

2. The kit according to claim 1, characterized in that said radio-opaque compound is zirconium dioxide.

3. The kit according to claim 1, characterized in that said radio-opaque compound is barium sulfate.

4. The kit according to claim 1, characterized in that the calcium phosphate is hydroxyapatite.

5. The kit according to claim 1, characterized in that it comprises in addition an effective quantity of one or more of the reagents selected from the group consisting of a chemical polymerization activator, a polymerization initiator and a stabilizer.

6. The kit according to claim 5, wherein the chemical polymerization activator is dimethylparatoluidine.

7. The kit according to claim 5, wherein the polymerization initiator is benzoyl peroxide.

8. The kit according to claim 5, wherein the stabilizer is hydroquinone.

9. A method of preparing a fluid cement for tilling the vertebral body, comprising mixing the powder components P and liquid components L according to claim 1 into a homogeneous mass in a weight ratio P/L between 1.4 and 1.6.

* * * * *